US009358008B2

(12) United States Patent
Mazzucco et al.

(10) Patent No.: US 9,358,008 B2
(45) Date of Patent: Jun. 7, 2016

(54) SURGICAL DEVICE

(71) Applicant: ZSX Medical, LLC, King of Prussia, PA (US)

(72) Inventors: Dan Mazzucco, Haddon Heights, NJ (US); Robert S. Cargill, II, West Deptford, NJ (US); Todd J. Kent, Cherry Hill, NJ (US); David George Reed, Langhorne, PA (US); Binh Bao Vu, Bristol, PA (US); Craig Hidalgo, Langhorne, PA (US)

(73) Assignee: ZSX Medical, LLC, King of Prussia, PA (US)

( * ) Notice: Subject to any disclaimer, the term of this patent is extended or adjusted under 35 U.S.C. 154(b) by 301 days.

(21) Appl. No.: 13/832,967

(22) Filed: Mar. 15, 2013

(65) Prior Publication Data

US 2013/0289586 A1 Oct. 31, 2013

Related U.S. Application Data

(60) Provisional application No. 61/640,306, filed on Apr. 30, 2012.

(51) Int. Cl.
*A61B 17/08* (2006.01)
*A61B 17/122* (2006.01)

(52) U.S. Cl.
CPC ............. *A61B 17/083* (2013.01); *A61B 17/122* (2013.01)

(58) Field of Classification Search
CPC .. A61B 17/0487; A61B 17/08; A61B 17/122; A61B 17/10; A61B 17/083

USPC ......... 606/142, 143, 151, 157, 158, 213, 214, 606/215, 216; 72/409.05; 24/489, 499, 500, 24/501, 519
See application file for complete search history.

(56) References Cited

U.S. PATENT DOCUMENTS

| 3,867,944 A | 2/1975 | Samuels |
| D277,785 S | 2/1985 | Green |

(Continued)

FOREIGN PATENT DOCUMENTS

| EP | 0714633 A1 | 6/1996 |
| WO | 2010126751 A1 | 11/2010 |

OTHER PUBLICATIONS

Int'l Search Report and Written Opinion issued Aug. 29, 2013 in Int'l Application No. PCT/US2013/037152.

(Continued)

*Primary Examiner* — Eric Rosen
*Assistant Examiner* — Mikail Mannan
(74) *Attorney, Agent, or Firm* — Panitch Schwarze Belisario & Nadel LLP (57) ABSTRACT

A wound closure device for closing a surgical wound includes at least one compressive clip for applying pressure to a patient's tissue. The clip includes a first clamping arm, a second clamping arm, and a flexible pin maintained between the first and second clamping arms in a press-fit relationship. Each of the first and second clamping arms has a proximal first end, an opposing distal second end and a sidewall extending therebetween. The clip has a first position in which the proximal first ends of the first and second clamping arms partially engage or do not engage each other and a second position in which the proximal first ends of the first and second clamping arms pivotally engage each other. In the second position of the clip, a compressive force generated at the proximal first ends is transferred through the first and second clamping arms to the distal second ends.

3 Claims, 5 Drawing Sheets

(56) References Cited

U.S. PATENT DOCUMENTS

| | | | |
|---|---|---|---|
| D283,642 S | 4/1986 | Gravener et al. | |
| D286,442 S | 10/1986 | Korthoff et al. | |
| 4,932,955 A | 6/1990 | Merz et al. | |
| 5,366,458 A | 11/1994 | Korthoff et al. | |
| 5,423,857 A | 6/1995 | Rosenman et al. | |
| 5,713,911 A | 2/1998 | Racenet et al. | |
| 5,713,912 A * | 2/1998 | Porter | A61B 17/128 606/151 |
| 6,165,204 A | 12/2000 | Levinson et al. | |
| 6,210,419 B1 | 4/2001 | Mayenberger et al. | |
| 6,261,303 B1 | 7/2001 | Mayenberger et al. | |
| 7,112,214 B2 | 9/2006 | Peterson et al. | |
| 7,699,860 B2 | 4/2010 | Huitema et al. | |
| 8,066,736 B2 | 11/2011 | Peterson et al. | |
| 8,075,481 B2 | 12/2011 | Park et al. | |
| 8,366,726 B2 | 2/2013 | Dennis | |
| 2002/0111641 A1 | 8/2002 | Peterson et al. | |
| 2004/0193185 A1 | 9/2004 | McBrayer | |
| 2005/0216036 A1 | 9/2005 | Nakao | |
| 2008/0004637 A1 * | 1/2008 | Klassen | A61B 17/122 606/142 |
| 2008/0300628 A1 | 12/2008 | Ellingwood | |
| 2010/0114133 A1 | 5/2010 | Huitema et al. | |
| 2011/0112559 A1 | 5/2011 | Monassevitch et al. | |
| 2011/0230900 A1 | 9/2011 | Sarradon | |
| 2011/0264118 A1 | 10/2011 | Mazzucco et al. | |

OTHER PUBLICATIONS

Int'l Preliminary Report on Patentability issued Nov. 13, 2014 in Int'l Application No. PCT/US2013/037152.
Supplemental Search Report issued Dec. 22, 2015 in EP Application No. 13784947.7.

* cited by examiner

SURGICAL DEVICE

CROSS-REFERENCE TO RELATED APPLICATIONS

This application claims the benefit of U.S. Provisional Patent Application No. 61/640,306, filed Apr. 30, 2012, entitled "Surgical Device," the entire disclosure of which is incorporated herein by reference.

BACKGROUND OF THE INVENTION

Existing methods and devices for creating and closing surgical incisions, particularly for surgical procedures involving soft tissue and internal organs, do not adequately protect patients from the associated health risks and complications, such as iatrogenic damage, ruptured organs, infections, and tissue adhesion. Further, the current technology does not significantly decrease the time necessary to carry out many types of surgical procedures. Thus, the existing methods and devices do not reduce the various risks directly related to the duration of a surgical procedure.

Prior art methods and devices of closing surgical incisions include, for example, sutures, staples, tapes, adhesives and energy-based sealants. However, these closure mechanisms are not sufficient prevention mechanisms against post-operative surgical site infections (SSI), the most common healthcare-associated infection in surgical patients. Patients who develop an SSI require significantly more medical care than those who are uninfected. For example, a surgical patient suffering from an SSI is 260 percent more likely to spend time in the intensive care unit after surgery than an uninfected patient. Further, an SSI increases the hospital length of stay for an infected patient by a median of two weeks. SSIs are particularly dangerous because they do not always develop immediately. Almost two percent of patients develop SSIs after they have been discharged from the hospital, and these patients are two to five times as likely to be readmitted to the hospital.

The prior art closure devices and methods suffer from several other deficiencies as well, particularly for certain types of procedures, such as those involving soft tissue and internal organs. Sutures may be risky because they can cause needlestick injury and subsequent infection to the medical personnel using them. Surgeons are also often faced with difficulty in repairing or closing incisions made for minimally-invasive surgeries, including laparoscopic procedures and natural orifice trans-lumenal endoscopic surgery (NOTES), which results in lengthened surgery times and/or incision sites that have not been sufficiently hermetically sealed. Prior art devices also often fail to achieve proper post-operative healing, and may result in unsightly permanent scarring. Further, for procedures requiring subsequent and repeated access to the incision site, such access is often difficult when the incision has been closed with prior art mechanisms. Finally, the prior art closure mechanisms often involve multi-stage procedures and, thus, an additional hospital visit is typically required for removal of the closure mechanism.

For these reasons, with respect to laparoscopic surgical procedures, and laparoscopic hysterectomies in particular, it is often difficult for surgeons to efficiently and effectively close incisions. Thus, there is an increase in the overall surgery time and an associated increase in the surgical risks and complications.

Thus, there is a need for a surgical wound closure device, particularly for laparoscopic surgical procedures, which enables medical personnel to efficiently and accurately close a surgical wound, thus decreasing the overall length of time for the surgical procedures and the risk of infection. There is a further need for a closure device for organs and tissue which have been cut or incised, thus resulting in a reduced risk of post-operative infections.

BRIEF SUMMARY OF THE INVENTION

In one embodiment, the present invention is directed to a wound closure device for closing a surgical wound. The device comprises at least one compressive clip for applying pressure to a patient's tissue. The clip comprises a first clamping arm, a second clamping arm, and a flexible pin maintained between the first and second clamping arms in an interference-fit relationship. Each of the first and second clamping arms has a proximal first end, an opposing distal second end and a sidewall extending therebetween. The distal second end of each of the first and second clamping arms is configured to contact the patient's tissue. The clip has a first position in which the proximal first ends of the first and second clamping arms partially engage or do not engage each other and a second position in which the proximal first ends of the first and second clamping arms pivotally engage each other. In the second position of the clip, a compressive force is generated at the proximal first ends of the first and second clamping arms and the generated compressive force is transferred through the first and second clamping arms to the distal second ends thereof.

In another embodiment, the present invention is directed to a wound closure device for closing a surgical wound. The device comprises at least one compressive clip for applying pressure to a patient's tissue. The clip comprises a first clamping arm and a second clamping arm, each of which has a proximal first end, an opposing distal second end and a sidewall extending therebetween. Each sidewall has an interior surface and an exterior surface, and the exterior surface of each sidewall generally extends in a first plane. At least one clamping tooth is provided at the distal second end of each the first and second clamping arms. The clamping tooth has a first leading surface, a second trailing surface opposed to the first leading surface, a base and a clamping tip opposed to the base. The leading surface generally extends at an angle of approximately 50° to 60° with respect to the first plane and the clamping tip generally extends at an angle of approximately 5° to 15° with respect to the first plane.

In another embodiment, the present invention is directed to a method of closing a surgical wound in a patient's tissue. The method comprises a step of providing at least one compressive clip. The clip comprises first and second clamping arms and a flexible pin maintained between the first and second clamping arms in an interference-fit relationship. Each of the first and second clamping arms has a proximal first end, an opposing distal second end and a sidewall extending therebetween. The distal second end of each of the first and second clamping arms is configured to contact the patient's tissue. The method further comprises the steps of positioning the at least one compressive clip in an expanded position on the patient's tissue and subsequently moving the at least one compressive clip to a contracted position. In the expanded position of the clip, the proximal first ends of the first and second clamping arms at least partially engage each other, the distal second ends of the first and second clamping arms are spaced apart from each other, the distal second end of the first clamping arm engages a first edge of the surgical wound and the distal second end of the second clamping arm engages a second opposing edge of the surgical wound. In the contracted position of the clip, the proximal first ends of the first and second clamping arms engage each other and distal second ends of the first and second clamping arms move toward each other and bring the edges of the surgical wound toward each other, such that a compressive force is generated at the proximal first ends of the first and second clamping arms and the generated compressive force is transferred through the first and second clamping arms to the distal second ends thereof and the patient's tissue.

BRIEF DESCRIPTION OF THE SEVERAL VIEWS OF THE DRAWINGS

The following detailed description of a preferred embodiment of the present invention will be better understood when read in conjunction with the appended drawings. For the purposes of illustrating the invention, there is shown in the drawings an embodiment which is presently preferred. It is understood, however, that the invention is not limited to the precise arrangements and instrumentalities shown. In the drawings.

DETAILED DESCRIPTION OF THE INVENTION

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the device and designated parts thereof. Unless specifically set forth herein, the terms "a", "an" and "the" are not limited to one element but instead should be read as meaning "at least one". The terminology includes the words noted above, derivatives thereof and words of similar import.

Figure 1A:
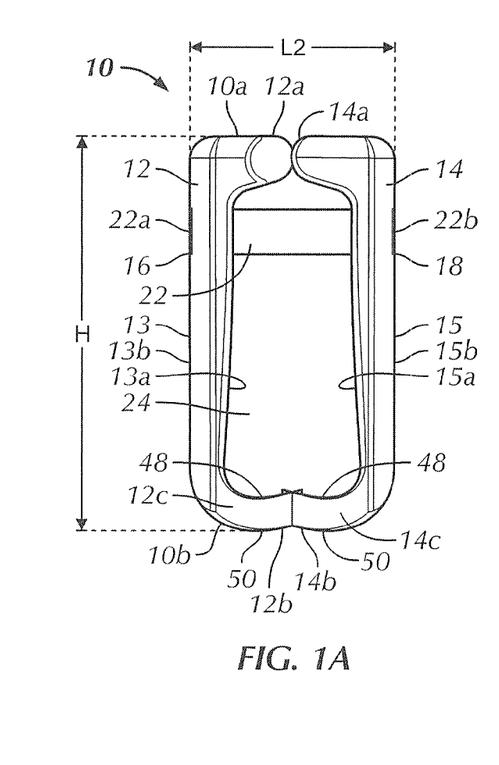
FIG. 1A is a front elevational view of a surgical device in accordance with a preferred embodiment of the present invention in an at-rest or starting position.

Referring to the drawings in detail, wherein like numerals and characters indicate like elements throughout, there is shown in FIGS. 1A-3B a presently preferred embodiment of a surgical device in accordance with the present invention. With reference initially to FIG. 1A, the surgical device preferably functions as a wound closure device, generally designated 10.

With particular reference to FIGS. 1A-1C and 3B, the wound closure device 10 preferably takes the form of a surgical compressive clip 10 which applies pressure to a patient's tissue 100, for example on both lateral sides of an incision, which causes hemostasis and/or brings together the two lateral sides of the incision. The clip 10 may be used to close incisions or other surgical wounds in bone, cutaneous tissue, subcutaneous tissue, including soft tissue, and internal organs. The clip 10 may be used for a surgical procedure performed on a human patient or for a veterinary or other surgical procedure. The clip 10 is particularly suited for closure of incisions made in internal tissue during a laparoscopic surgical procedure, in which relatively small sized skin incisions of less than 2 centimeters are made. More particularly, the clip 10 is well suited for use in laparoscopic hysterectomy procedures, in which small sized incisions of approximately 7 to 15 mm are made. However, it will be appreciated that the clip 10 is appropriate for use in any type of surgical procedure. Also, while the internal tissue of a human patient is generally referred to herein for illustrative purposes, it will be apparent to one of ordinary skill in the art that the clip 10 may be employed on various types of tissue, such as cutaneous tissue, and on any internal organ, such as a kidney, lung, liver, heart, muscle, connective tissue, etc., and on various types of animal patients.

In one embodiment, a plurality of clips 10 may be used for applying pressure to a patient's tissue 100 (for example at laterally spaced locations along the length of an incision) for closure of incised tissue. While the term "clip" is used herein to describe the wound closure device 10, it will be understood by those skilled in the art that the clip 10 essentially functions as a clamp, and thus may be referred to as a clamp or any other appropriate name.

The clip 10 is preferably a compressive clip having an elongated shape and comprises a first clamping arm 12 and a second clamping arm 14. In one embodiment, the clip 10 is preferably a hemostatic clip. Each clamping arm 12, 14 is preferably a one-piece component, and more preferably a one-piece molded component. The first clamping arm 12 has a proximal first end 12a, an opposing distal second end 12b, and a sidewall 13 extending from the proximal end 12a to the distal end 12b. The second clamping arm 14 has a proximal first end 14a, an opposing distal second end 14b, and a sidewall 15 extending from the proximal end 14a to the distal end 14b. The proximal first ends 12a, 14a of the first and second clamping arms 12, 14 generally define a top 10a of the clip 10. The distal second ends 12b, 14b of the first and second clamping arms 12, 14 generally define a bottom 10b of the clip 10.

Each sidewall 13, 15 has a first, interior surface 13a, 15a and an opposing second exterior surface 13b, 15b. Preferably, the sidewalls 13, 15 taper inwardly from the top 10a of the clip 10 toward the bottom 10b of the clip 10. More particularly, the sidewalls 13, 15 are thicker proximate the top 10a of the clip 10 than they are proximate the bottom 10b of the clip 10. However, it will be understood that the sidewalls 13, 15 of the first and second clamping arms 12, 14 may have a uniform thickness from the top 10a of the clip to the bottom 10b of the clip 10 or may taper outwardly from the top 10a of the clip 10 toward the bottom 10b of the clip 10. It will also be understood that the sidewalls 13, 15 of the first and second clamping arms 12, 14 may have any thickness, as long as they maintain the desired shape during and/or after application of the clip 10 to a patient's tissue 100.

Figure 2A:
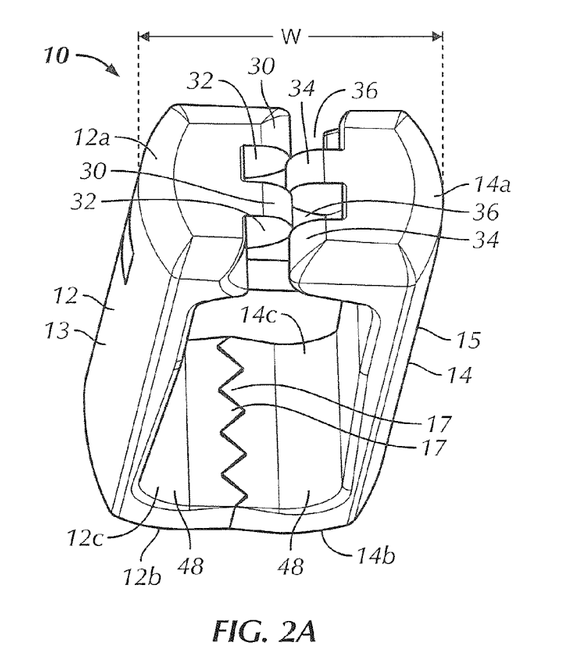
FIG. 2A is a top isometric view of the surgical device shown in FIG. 1A in the at-rest position.
Figure 2B:
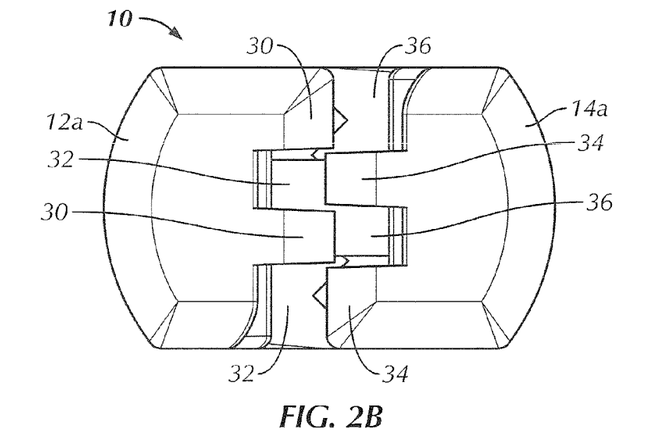
FIG. 2B is a top plan view of the surgical device shown in FIG. 2A.

Preferably, the proximal first ends 12a, 14a of the first and second clamping arms 12, 14 are removably connectable or engageable with each other. In one embodiment, as shown in FIGS. 2A-2B, the proximal first end 12a of the first clamping arm 12 includes a plurality of tabs or protrusions 30 and slots or sockets 32, and the proximal first end 14a of the second clamping arm 14 includes a plurality of tabs or protrusions 34 and slots or sockets 36. The protrusions 30 of the proximal first end 12a of the first clamping arm 12 are removably engageable with the sockets 36 of the proximal first end 14a of the second clamping arm 14, and the protrusions 34 of the proximal first end 14a of the second clamping arm 14 are removably engageable with the sockets 32 of the proximal first end 12a of the first clamping arm 12.

The distal second end 12b of the first clamping arm 12 preferably comprises a first clamping edge 12c and the distal end 14b of the second clamping arm 14 preferably comprises a second clamping edge 14c. Each of the first and second clamping edges 12c, 14c has a first or upper surface 48, which is a leading surface, and an opposed second or lower surface 50, which is a trailing surface. It will be understood by those skilled in the art that alternative designations for the first and second surfaces 48, 50 of the clamping edges 12c, 14c are also appropriate. When the clip 10 is arranged on a patient's tissue 100, as shown in FIG. 3B, the first and second clamping edges 12c, 14c engage and clamp the patient's tissue 100, as described more fully herein.

Figure 1B:
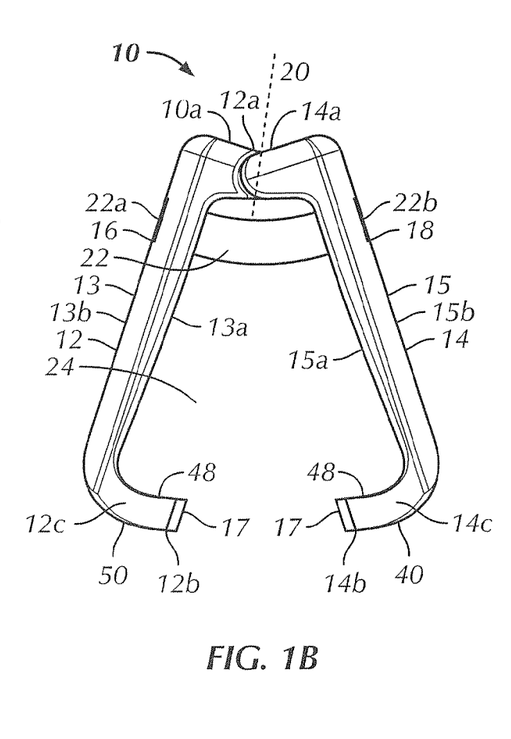
FIG. 1B is a front elevational view of the surgical device shown in FIG. 1A in an expanded position.
Figure 1C:
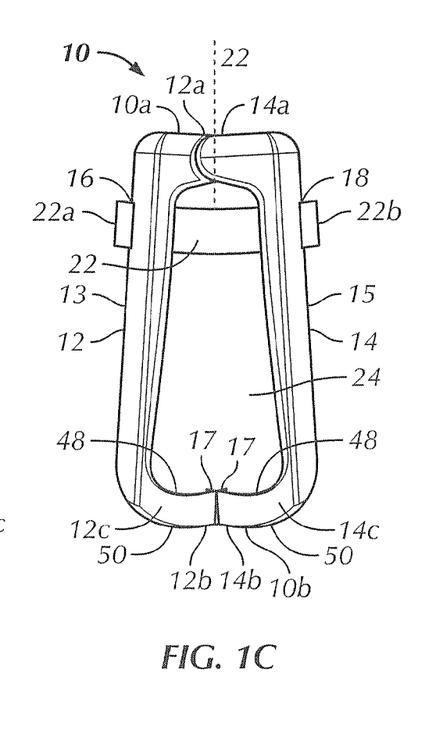
FIG. 1C is a front elevational view of the surgical device shown in FIG. 1A in a contracted position.

As shown in FIGS. 1A-1C, the first clamping edge 12c of the first clamping arm 12 preferably extends inwardly from the sidewall 13 toward an internal cavity 24 of the clip 10. Similarly, the second clamping edge 14c of the second clamping arm 14 preferably extends inwardly from the sidewall 15 of the second clamping arm 14 toward the internal cavity 24 of the clip 10. More preferably, the first and second clamping edges 12c, 14c extend arcuately and inwardly from the respective sidewalls 13, 15 toward the internal cavity 24 and the top 10a of the clip 10. As such, the leading and trailing surfaces 48, 50 of the first and second clamping edges 12c, 14c are preferably arcuate, and more preferably concave, in shape with respect to the top 10a of the clip 10.

The distal second ends 12b, 14b of the first and second clamping arms 12, 14 preferably further comprise at least two, and more preferably a plurality of spaced-apart clamping teeth 17. More particularly, at the distal second ends 12b, 14b, a plurality of spaced-apart clamping teeth 17 preferably extend from the first and second clamping edges 12c, 14c to directly contact and clamp the patient's tissue 100. The spaced-apart teeth 17 preferably extend along at least a portion of the length of the respective clamping edge 12c, 14c, but more preferably along the entire length of the respective clamping edge 12c, 14c. In one embodiment, three to four spaced-apart clamping teeth 17 are preferably formed at each of the first and second clamping edges 12c, 14c. However, it will be understood by those skilled in the art that the number of clamping teeth 17 may vary depending upon the particular type of tissue to be clamped in order to optimize the structure of the clip 10 for specific procedures.

Figure 4:
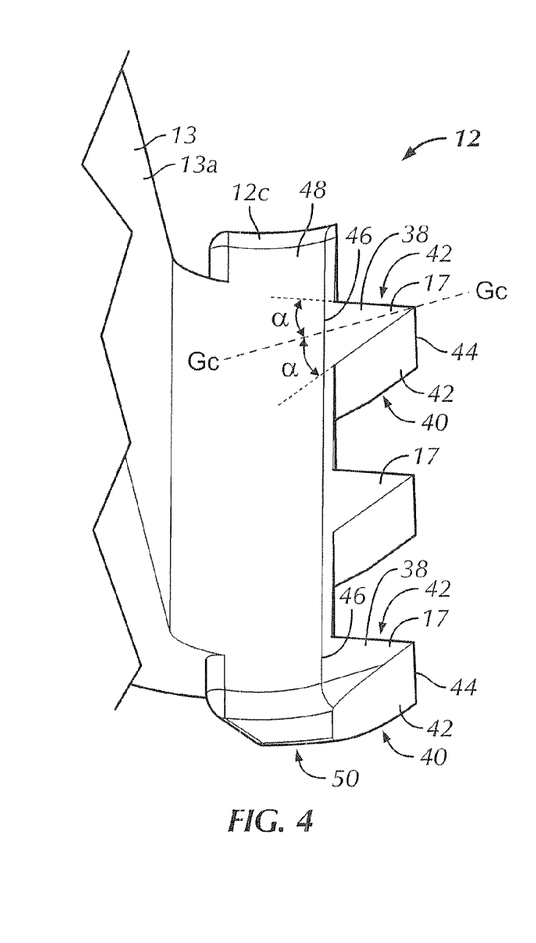
FIG. 4 is an enlarged isometric view of the teeth of a surgical device in accordance with a preferred embodiment of the present invention.

Referring to FIG. 4, each of the clamping teeth 17 preferably has a first or upper surface 38, an opposed second or lower surface 40, a pair of opposed lateral side surfaces 42 extending between the first surface 38 and the second surface 40, a clamping tip 44 and an opposing base 46. The base 46 of each tooth 17 is generally aligned with a distal edge of each of the first and second clamping edges 12c, 14c. The first surface 38 is described hereinafter as a leading surface and the second surface 40 is described hereinafter as being a trailing surface. However, it will be understood by those skilled in the art that alternative designations for the first and second surfaces are also appropriate.

The opposing lateral side surfaces 42 of each tooth 17 are preferably generally planar surfaces which extend from the base 46 and taper toward each other to form the clamping tip 44. More preferably, the inwardly tapered lateral side surface 42 of each tooth 17 extends at an angle $\alpha$, of approximately 15° to 30°, and more preferably approximately 20°, with respect to a geometric centerline $G_c$ of the tooth 17.

The leading surface 38 of each tooth 17 is preferably generally aligned with and extends from the leading surfaces 48 of the first and second clamping edges 12c, 14c. Similarly, the trailing surface 40 of each tooth 17 is preferably generally aligned and extends from the trailing surfaces 50 of the first and second clamping edges 12c, 14c. Thus, the distal second end 12b, 14b of each of the first and second clamping arms 12, 14, as defined by the curved clamping edges 12c, 14c and the clamping teeth 17 extending therefrom, has a generally hook-like shape.

It will be understood that the degree of curvature of the distal second ends 12b, 14b may vary depending upon, for example, the particular type of tissue to be clamped in order to optimize the structure of the clip 10 for specific procedures. For example, in one embodiment, shown in FIGS. 1A-1C, the distal second ends 12b, 14b are only slightly curved or concave, such that the first and second clamping edges 12c, 14c are almost generally perpendicular to the sidewalls 13, 15 of the first and second clamping arms 12, 14. However, in another embodiment, as shown in FIG. 5, the distal second ends 12b, 14b are more pronouncedly arcuate, such that the clamping teeth 17 are decidedly angled upwardly with respect to the sidewalls 13, 15 of the respective first and second clamping arms 12, 14 toward the top 10a of the clip 10.

Figure 5:
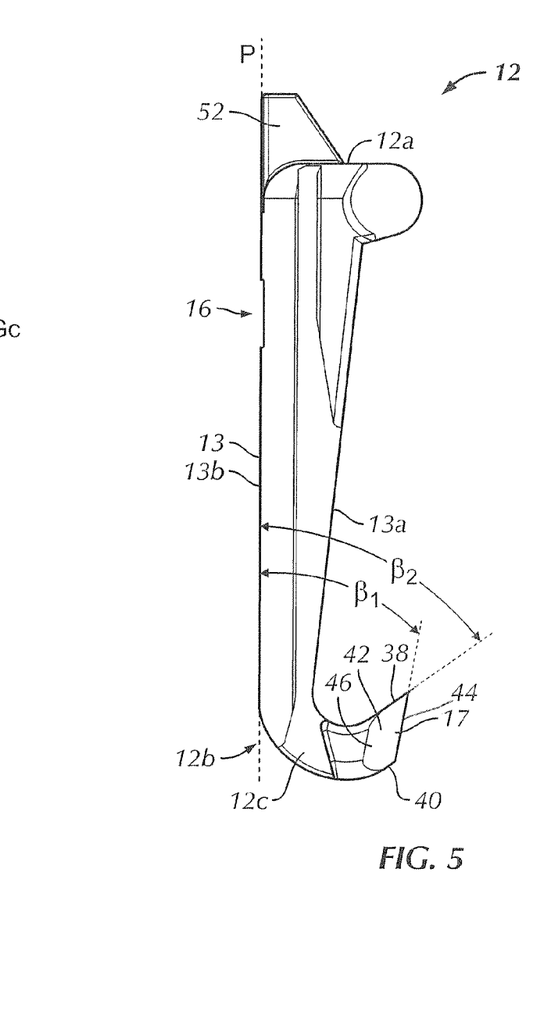
FIG. 5 is an enlarged front elevational view of one arm of a surgical device in accordance with a preferred embodiment of the present invention.
Figure 6:
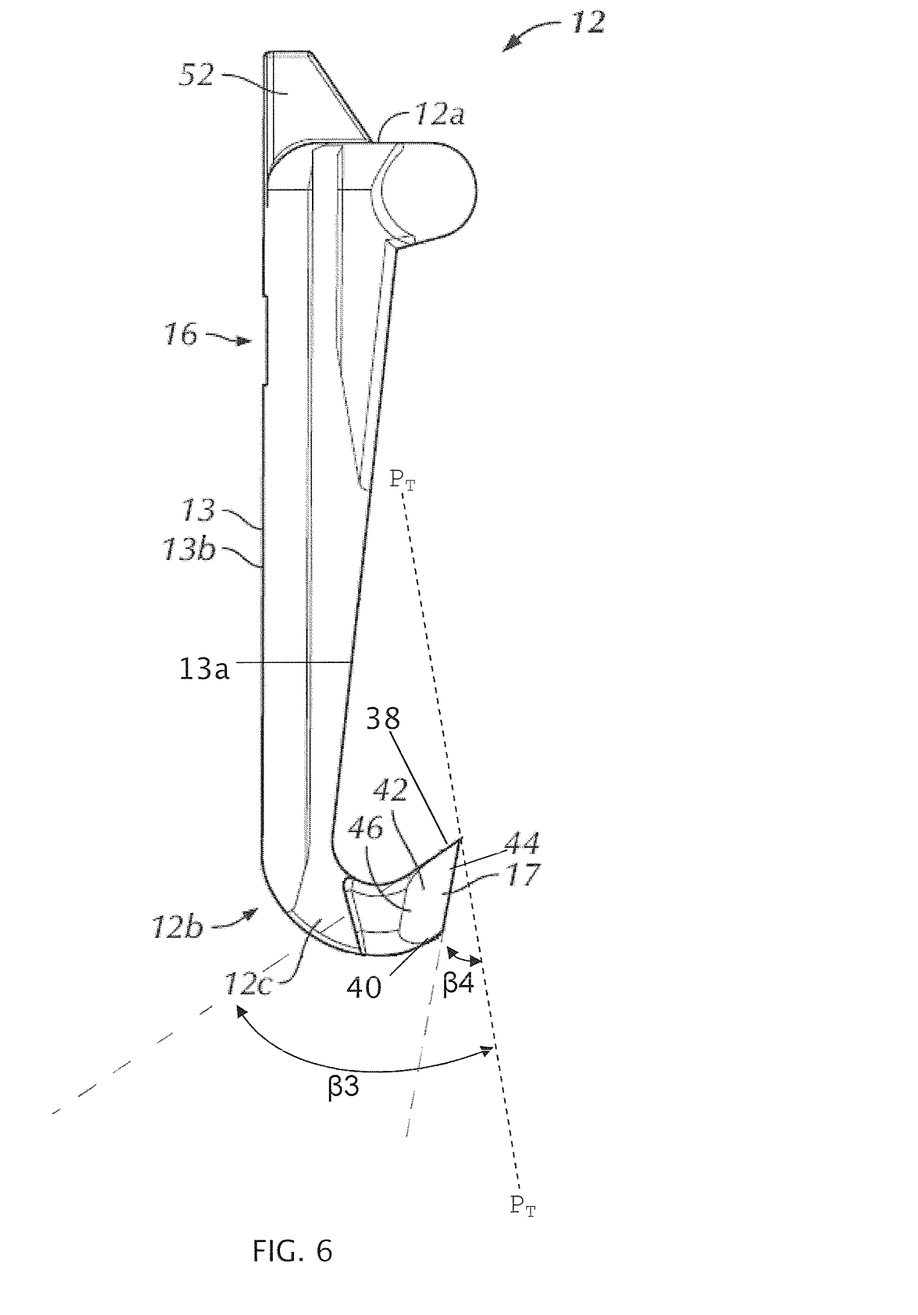
FIG. 6 is an enlarged front elevational view of the arm shown in FIG. 5 when in contact with a patient's tissue.

More particularly, in one embodiment, as shown in FIGS. 5-6, each clamping tooth 17 preferably has an arcuate cross-sectional shape. Referring to FIG. 5, in a preferred embodiment, the exterior surface 13b, 15b of the sidewall 13, 15 of each clamping arm 12, 14 generally defines a base plane P, and each tooth 17 is formed such that the clamping tip 44 generally extends at an angle $\beta_1$ of approximately 5° to 15°, and more preferably at an angle $\beta_1$ of approximately 10° with respect to the base plane P. Also, in such an embodiment, the leading surface 38 generally extends at an angle $\beta_2$ of approximately 50° to 60°, and more preferably at an angle $\beta_2$ of approximately 55° with respect to the base plane P. The base 46 of each tooth preferably extends at generally the same angle $\beta_1$ as the clamping tip 44 and the trailing surface 40 of each tooth preferably extends at generally the same angle $\beta_2$ as the leading surface 38.

Referring to FIG. 6, when the teeth 17 are formed as shown in FIG. 5, each tooth 17 preferably contacts the patient's tissue 100 at a predetermined angle. More particularly, the patient's tissue 100 generally defines a plane $P_T$ and the leading surface 38 of each tooth 17 preferably extends at an angle $\beta_3$ of approximately 60° to 75°, and more preferably at an angle $\beta_3$ of approximately 75°, with respect to the plane $P_T$ of the patient's tissue 100. The clamping tip 44 of each tooth 17 preferably extends at an angle $\beta_4$ of approximately 15° to 30°, and more preferably at an angle $\beta_4$ of approximately 15°, with respect to the plane $P_T$ of the patient's tissue 100. The trailing surface 40 of each tooth preferably extends at generally the same angle $\beta_3$ as the leading surface 38 and the base 46 of each tooth preferably extends at generally the same angle $\beta_4$ as the clamping tip 44 with respect to the plane $P_T$ of the patient's tissue 100.

It will be understood by those skilled in the art that the form, amplitude, and period of the clamping teeth 17 may vary depending upon the particular type of tissue to be clamped in order to optimize the structure of the clip 10 for specific procedures. It will also be understood that the first and second clamping ends 12b, 14b need not have any clamping teeth 17 and instead may be formed of only the first and second clamping edges 12c, 14c.

It will also be understood by those skilled in the art that the first and second clamping edges 12c, 14c need not extend in an arcuate fashion from the sidewalls 13, 15. Instead, in one embodiment, the first and second clamping edges 12c, 14c may extend generally perpendicularly from the sidewalls 13, 15 toward the internal cavity 24. In such an embodiment, the clamping teeth 17 may also extend generally perpendicularly with respect to the sidewalls 13, or, alternatively, may extend arcuately and upwardly from the first and second clamping edges 12c, 14c toward the top 10a of the clip 10.

Preferably, the first and second clamping arms 12, 14 are separate and distinct components which are connected to each other, as described more fully below. However, it will be appreciated by those skilled in the art that the clip 10 need not be formed by two separate and connected clamping arms 12, 14. For example, in another embodiment, the clip 10 may be a one-piece clip (not shown) with a living hinge connecting first and second clamping arms 12, 14.

In one embodiment, the clip 10 includes a support bar or pin 22 disposed at a position spaced apart from the distal second ends 12b, 14b of the first and second clamping arms 12, 14. More preferably, the clip 10 includes a generally flexible pin 22 spaced apart from the distal second ends 12b, 14b and maintained between the first and second clamping arms 12, 14 with a friction fit, interference fit or press fit relationship. In a preferred embodiment, the pin 22 is preferably spaced approximately 10 mm away from the distal second ends 12b, 14b of the first and second clamping arms 12, 14 and extends between the first and second clamping arms 12, 14 in a direction generally perpendicular to the longitudinal axis $X_1$ of the clip 10.

For purposes of clarity, the pin 22 is described hereinafter and in the claims as being maintained between the first and second clamping arms 12, 14 in an interference fit relationship. However, it will be understood by those skilled in the art that the term "interference fit," as used hereinafter and in the claims, may mean any one of friction fit, interference fit or press fit.

A description of the structure and configuration of a preferred embodiment of the interference fit pin 22 and the first and second clamping arms 12, 14 is now provided.

A first aperture 16 is formed in the body of the first clamping arm 12, and more particularly in the sidewall 13 of the first clamping arm 12, at a position between and spaced apart from the proximal first end 12a and the distal second end 12b. A second aperture 18 is formed in the body of the second clamping arm 14, and more particularly in the sidewall 15 of the second clamping arm 14, at a position between and spaced apart from the proximal first end 14a and the distal second end 14b. The position of the first aperture 16 generally corresponds to and is generally aligned with that of the second aperture 18, such that the first and second apertures 16, 18 are generally directly opposed from each other. It will be appreciated that the first and second apertures 16, 18 may be formed at any position along the longitudinal axis $X_1$ of the clip 10. Preferably, the first and second apertures 16, 18 are spaced approximately 10 mm away from the distal second ends 12b, 14b of the first and second clamping arms 12, 14.

In such an embodiment, a first end 22a of the pin 22 is received within the first aperture 16 of the first clamping arm 12 and a second end 22b of the pin 22 is received within the second aperture 18 of the second clamping arm 14. As such, the pin 22 extends between the first and second clamping arms 12, 14 in a direction generally perpendicular to the longitudinal axis X of the clip 10. The pin 22 also preferably includes fillets to reduce stress risers.

Preferably, each of the first and second ends 22a, 22b of the pin 22 has a cross-sectional area that is at least slightly larger than that of the first and second apertures 16, 18, such that the pin 22 is maintained between the first and second clamping arms 12, 14 with an interference fit relationship. More particularly, the first end 22a of the pin 22 is preferably interference fit in the first aperture 16 of the first clamping arm 12 and the second end 22b of the pin 22 is preferably interference fit in the second aperture 18 of the second clamping arm 14. As such, the pin 22 connects the first and second clamping arms 12, 14.

In one embodiment, the pin 22 preferably has a uniform cross-sectional area. For example, the pin may have a uniform thickness of approximately 2.05 mm, while the height of each of the first and second apertures 16, 18 is approximately 2 mm. In another embodiment, the pin 22 may have a varying thickness, as long as the first and second ends 22a, 22b of the pin 22 may be interference fit with the first and second apertures 16, 18. For example, the cross-sectional area of the pin 22 may be at least slightly larger at the first and second ends 22a, 22b and taper towards the center of the pin 22. Thus, for example, if the height of each of the first and second apertures 16, 18 is approximately 2 mm, the first and second ends 22a, 22b of the pin 22 may have a thickness of approximately 2.05 mm while the remainder of the pin 22 has a thickness of approximately 2 mm.

Preferably, the pin 22, the first aperture 16, and the second aperture 18 each have a generally square or rectangular cross-sectional shape. However, it will be understood by those skilled in the art that the pin 22 and the first and second apertures 16, 18 may have any cross-sectional shape, such as circular, elliptical, triangular, trapezoidal and the like, as long as the cross sectional shape of the pin 22 and the first and second apertures 16, 18 enable the pin 22 to be received within the first and second apertures 16, 18 in an interference fit.

It will be understood by those skilled in the art that the above description relates to just one possible configuration of the pin 22, and that numerous other configurations are possible as long as the pin 22 is maintained between the first and second clamping arms 12, 14 in an interference fit. For example, in one embodiment (not shown), one end of the pin 22 may be integrally formed with one of the sidewalls 13, 15 of the first and second clamping arms 12, 14 and the other end of the pin 22 may be configured to contact the other of the sidewalls 13, 15, so as to maintain the pin 22 in an interference fit relationship therebetween. In another embodiment (not shown), the pin 22 may act as a rivet, such that after the first and second ends 22a, 22b of the pin 22 pass through the first and second apertures 16, 18, the material of the first and second ends 22a, 22b is plastically deformed so as to lock the pin 22 in place.

Preferably, at least a portion of the first and second clamping arms 12, 14 and the flexible pin 22 of the clip 10 is made from a material which is bio-absorbable and may be made of a material that is absorbable by human or animal tissue, and resistant to the formation of tissue adhesions. More preferably, the entirety of each of the first and second clamping arms 12, 14 and the pin 22 of the clip 10 is made from such a bio-absorbable material. For example, the first and second clamping arms 12, 14 and the pin 22 may be made of hyaluronic acid, carboxymethylcellulose, hydrolytically-degradable polyester urethane, oxidized regenerated cellulose, poly glycolic acid (PGA), poly lactic acid (PLA), poly malic acid, poly (isobutyl cyanoacrylate), poly-p-dioxanone (PDO), poly (trimethylene carbonate) (TMC), poly caprolactone (PCL), nucleic acids, collagen, chitosan, fibrin, or other polypeptides, or any combination or copolymer thereof. Preferably, the first and second clamping arms 12, 14 and the pin 22 are made of PDO and, more preferably, of a middle molecular weight PDO. It will be understood by those skilled in the art that the first and second clamping arms 12, 14 and the pin 22 may be made of any appropriate bio-absorbable material or biologic material.

The clip 10 is expandable and retractable, and preferably has at least three positions: an at-rest (initial or starting) position (as shown in FIG. 1A), an expanded (pre-use or intermediate) position (as shown in FIG. 1B), and a contracted (use) position (as shown in FIG. 1C). In the at-rest position, the proximal first ends 12a, 14a of the first and second clamping arms 12, 14 are generally unengaged, separated and/or or least slightly spaced apart from each other and the interior cavity 24 of the clip 10 has a generally rectangular or square shaped cross section. However, it will be understood that the proximal first ends 12a, 14a of the first and second clamping arms 12, 14 may slightly partially engage each other. Preferably, the pin 22 is generally straight or linear along its entire length L1.

In the embodiment where the pin 22 is held within the first and second apertures 16, 18, the first and second ends 22a, 22b, of the pin 22 are generally flush with the respective exterior surfaces 13b, 15b of the sidewalls 13, 15 of the first and second clamping arms 12, 14 in the at-rest position. However, it will be appreciated that the first and second ends 22a, 22b of the pin 22 may extend through the first and second apertures 16, 18 and at least slightly outwardly away from the exterior surfaces 13b, 15b of the sidewalls 13, 15 of the first and second clamping arms 12, 14.

Preferably, in the at-rest position, when the clip 10 is not yet positioned on the patient's tissue 100, the distal second ends 12b, 14b of the first and second clamping arms 12, 14 contact or engage each other. However, it will be appreciated that a slight gap may exist between the distal second ends 12b, 14b. Preferably, in the at-rest position of the clip 10, the plurality of teeth 17 of the first and second clamping arms 12, 14 engage each other in an interlocking fashion (see FIG. 2A).

Also, in the at-rest position, the overall dimensions of the clip 10 are such that the clip 10 is configured to be received or stored within and pass through a tube or chamber of a laparoscopic tool, which typically has a diameter of only a few millimeters and, more particularly, approximately 10 millimeters. For example, the clip 10 may have an overall width W of approximately 9.5-10 millimeters, and an overall height H of approximately 15 millimeters. However, it will be appreciated that the dimensions of the clip 10 may vary based on the particular laparoscopic tool being used and the size of the particular incision to be closed. Likewise, the clip 10 may have an overall length L1 of approximately 15 mm, but it will be appreciated that the length of the clip 10 may vary based on the size of the particular incision to be closed.

Figure 3A:
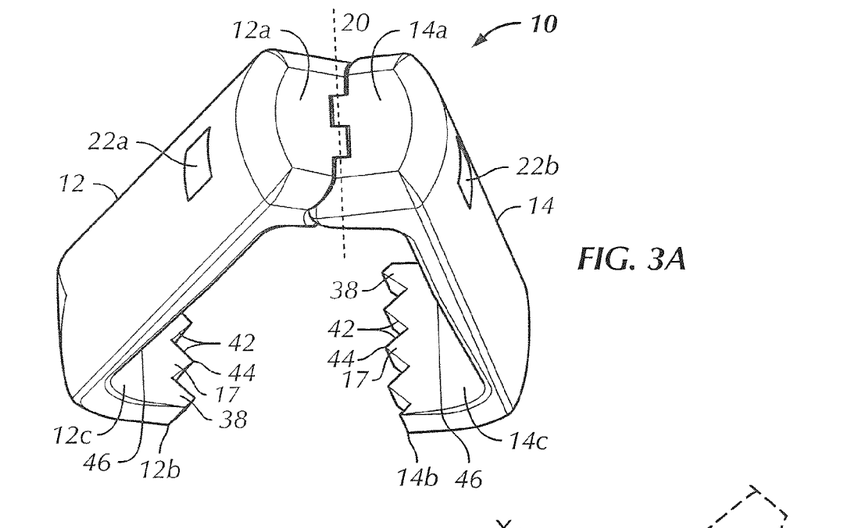
FIG. 3A is a top isometric view of the surgical device shown in FIG. 1A in the expanded position.
Figure 3B:
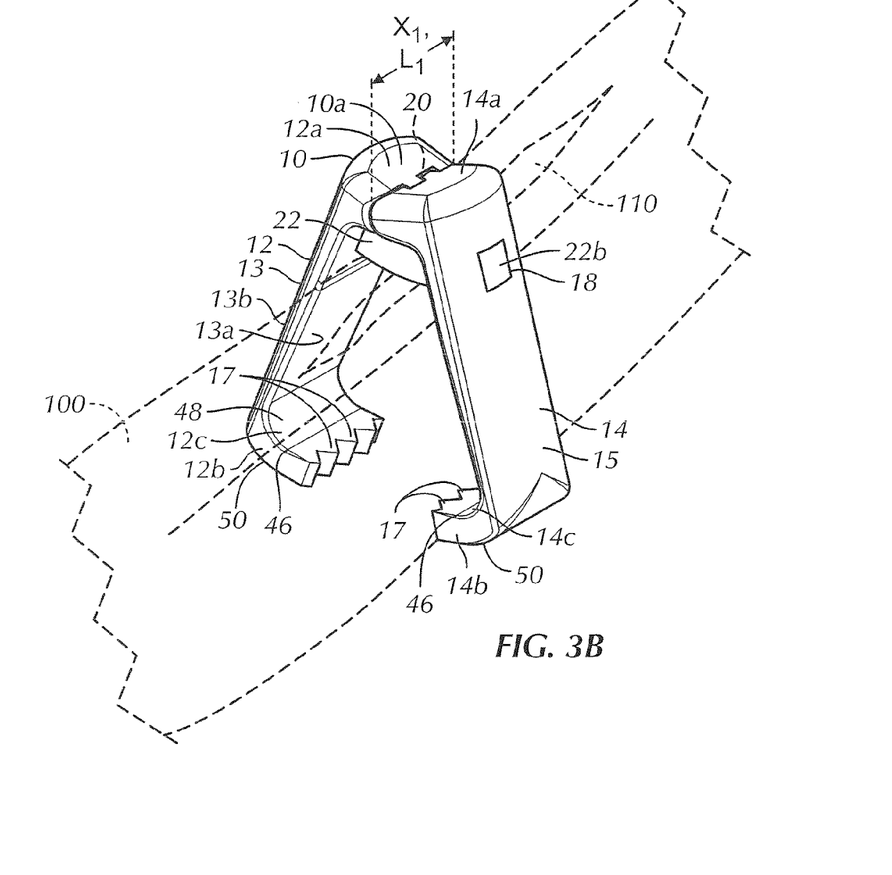
FIG. 3B is a side isometric view of the surgical device shown in FIG. 3A positioned on a patient's tissue.

In the expanded position of the clip 10, as shown in FIGS. 1B and 3A-3B, the proximal first ends 12a, 14a of the first and second clamping arms 12, 14 are moved toward each other such that the proximal first ends 12a, 14a at least partially contact or engage each other. In a preferred embodiment, the partial engagement of the proximal first ends 12a, 14a is effected by the protrusions 30 of the proximal first end 12a of the first clamping arm 12 being at least partially received within the sockets 36 of the proximal first end 14a of the second clamping arm 14, and the protrusions 34 of the proximal first end 14a of the second clamping arm 14 being at least partially received within the sockets 32 of the proximal first end 12a of the first clamping arm 12. However, it will be understood that engagement of the proximal first ends 12a, 14a may be achieved by any known conventional mechanisms.

In the expanded position of the clip 10, the partial engagement of the proximal first ends 12a, 14a of the first and second clamping, arms 12, 14 approximates or emulates that of a fixed pivot. Thus, in the expanded position of the clip 10, the proximal first ends 12a, 14a of the first and second clamping arms 12, 14 are at least partially engaged with each other via a virtual fixed hinge or pivot 20.

While the proximal first ends 12a, 14a of the first and second clamping arms 12, 14 are brought together into at least partial contact with each other in the expanded position, the distal second ends 12b, 14b (i.e., the first and second clamping edges 12c, 14c and the associated teeth 17) of the first and second clamping arms 12, 14 are spaced apart from each other, such that the interior cavity 24 of the clip 10 has a generally V-shaped cross section. In the expanded position, the clip 10 preferably spans a gap of approximately 10 millimeters from the distal second end 12b of the first clamping arm 12 to the distal second end 14b of the second clamping arm 14. It should be appreciated by those skilled in the art that the size of the gap between the distal second ends 12b, 14b of the first and second clamping arms 12, 14 may be larger or smaller in the expanded position, depending upon the size of the clip 10 as well as other factors, such as the size of the wound or incision to be closed.

Also, in the expanded position of the clip 10, the flexible pin 22 has transitioned to a first generally arcuate or curved cross-sectional shape, in which the flexible pin 22 is at least slightly curved with respect to the top 10a of the clip 10, as shown in FIG. 1B. More particularly, the first and second ends 22a, 22b of the pin 22 curve upwardly toward the top 10a of the clip 10. The first and second ends 22a, 22b of the pin 22 remain generally flush with the respective exterior surfaces 13b, 15b of the sidewalls 13, 15 of the first and second clamping arms 12, 14. However, in the embodiment where the pin 22 is held within the first and second apertures 16, 18, it will be appreciated that the first and second ends 22a, 22b of the pin 22 may extend through the first and second apertures 16, 18 and at least slightly outwardly away from the exterior surfaces 13b, 15b of the sidewalls 13, 15 of the first and second clamping arms 12, 14. The interference-fit relationship of the flexible pin 22 and the first and second clamping arms 12, 14, and more particularly the force generated by the flexed or arcuate interference-fit pin 22, helps maintains the clip 10 in the expanded position.

More particularly, as the proximal first ends 12a, 14a of the first and second clamping arms 12, 14 are moved or pivoted toward each other at the top 10a of the clip 10 and the first and second clamping edges 12c, 14c are spread apart from each other at the bottom 10b of the clip 10, the interference-fit flexible pin 22 naturally transitions to a generally curve arcuate shape to facilitate spreading apart of the first and second clamping edges 12c, 14c and the teeth 17. Because the pin 22 engages the first and second clamping arms 12, 14 in an interference fit, the flexed or arcuate pin 22 generates and exerts sufficient force to allow the clip 10 to remain in the expanded position through friction and prevents the clip 10 from automatically transitioning to the at-rest position to which it is biased.

In the contracted position of the clip 10, as shown in FIG. 1C, the proximal first ends 12a, 14a and the distal second ends 12b, 14b (i.e., first and second clamping edges 12c, 14c and the teeth 17) of the first and second clamping arms 12, 14 are moved or pivoted toward each other. More preferably, the proximal first ends 12a, 14a of the first and second clamping arms 12, 14 are moved toward each other, such that the proximal first ends 12a, 14a directly contact or engage each other about the virtual hinge or pivot 20. In a preferred embodiment, the direct pivotal engagement of the proximal first ends 12a, 14a is effected by the protrusions 30 of the proximal first end 12a of the first clamping arm 12 being generally completely received within the sockets 36 of the proximal first end 14a of the second clamping arm 14, and the protrusions 34 of the proximal first end 14a of the second clamping arm 14 being generally completely received within the sockets 32 of the proximal first end 12a of the first clamping arm 12. However, it will be understood that the pivotal engagement of the proximal first ends 12a, 14a may be achieved by alternative known conventional mechanisms.

Also, when the clip 10 is in the contracted position, but not arranged on the patient's tissue 100, the distal second ends 12b, 14b of the first and second clamping arms 12, 14 directly contact or engage each other. Preferably, in the contracted position of the clip 10, when the clip 10 is not placed on the patient's tissue 100, the plurality of teeth 17 of the first and second clamping arms 12, 14 engage each other in an interlocking fashion (as shown in FIG. 1C). When the clip 10 is placed on the patient's tissue 100 for closure of an incision, as described more fully below, the plurality of teeth 17 engage and clamp the tissue 100 together, thereby effectively promoting tissue healing at the site of the incision. The clamping teeth 17 provide the additional advantage of helping to anchor the clip 10 to the tissue 100.

In the embodiment where the pin 22 is held within the first and second apertures 16, 18, because the proximal first ends 12a, 14a of the first and second clamping arms 12, 14 have been brought into direct engagement with each other in the contracted position, the first and second ends 22a, 22b, of the pin 22 are no longer flush with the exterior surfaces 13b, 15b of the sidewalls 13, 15 of the first and second clamping arms 12, 14. Instead, at least one of the first or second ends 22a, 22b, of the pin 22 extend through at least one of the first or second apertures 16, 18 and outwardly away from at least one of the exterior surfaces 13b, 15b of the sidewalls 13, 15 (as shown in FIG. 1C).

In the contracted position, the pivotally engaged first and second clamping arms 12, 14 generate a force which is translated or transferred through the first and second clamping edges 12c, 14c to the patient's tissue 100 in contact with the first and second clamping edges 12c, 14c. More particularly, in this position, a clamping force is generated at the top 10a of the clip 10, and specifically at the proximal first ends 12a, 14a of the first and second clamping arms 12, 14, remotely from the patient's tissue 100. This force is then translated or transferred through the sidewalls 13, 15 of the first and second clamping arms 12, 14 to the distal second ends 12b, 14b, and more particularly to the first and second clamping edges 12c, 14c, the clamping teeth 17, and ultimately to the patient's tissue 100.

Because the pin 22 is maintained in an interference-fit relationship between the first and second clamping arms 12, 14 spaced apart from the distal second ends 12b, 14b, which are in contact with the patient's tissue, the compressive force is generated remotely from the surface tissue and is able to be translated across the incised tissue 100 to a depth below the surface tissue. If the force were generated at and applied only to the surface tissue, the tissue 100 could not be clamped to a satisfactory degree, since the surface tissue is essentially dead and will eventually slough off.

Referring to FIG. 3B, during a surgical procedure, the clip 10 is attached to a patient's tissue 100 in an area of the tissue 100 having an incision 110 which is to be closed. When the clip 10 is used for a laparoscopic surgery, such as a laparoscopic hysterectomy, a surgeon first makes one or more small incisions in the patient's subcutaneous tissue 100 and then uses various laparoscopic instruments to perform the surgical procedure. Once the procedure is completed, the surgeon uses one or more laparoscopic tools or applicators for positioning and clamping the clip 10 (or a plurality of clips 10) on the incised tissue 100.

For example, in one embodiment, the surgeon positions a cannula (not shown) within the incised tissue 100. As will be appreciated by those skilled in the art, laparoscopic cannulas are thin, hollow, flexible tubes having in interior diameter of approximately 10 millimeters. The clip 10 is positioned within the cannula in its at-rest position. The surgeon then utilizes a laparoscopic tool (not shown) to facilitate passage of the clip 10 through the cannula. While within the cannula, the clip 10 remains in its at-rest position. Once the clip 10 is advanced through the cannula, the surgeon utilizes the laparoscopic tool to properly position the clip 10 and transition the clip 10 into the expanded position. To transition the clip 10 into the expanded position, the surgeon preferably uses the laparoscopic tool (or some other tool) to apply force or pressure to the proximal first ends 12a, 14a of the first and second clamping arms 12, 14 so as to force the proximal first ends 12a, 14a toward each other. This, in turn, forces the distal second ends 12b, 14b of the first and second clamping arms 12, 14 to spread apart or away from each other and forces the pin 22 to transition to its first arcuate or flexed configuration.

The surgeon may also use a tool to apply an outward-directed force at or near the distal second ends 12b, 14b of the first and second clamping arms 12, 14 to further force the distal second ends 12b, 14b of the first and second clamping arms 12, 14 to spread apart or away from each other and to further force the pin 22 to transition to its first arcuate or flexed configuration.

Preferably, as shown in FIG. 5, a knob 52 protrudes upwardly away from each of the proximal first ends 12a, 14a of the first and second clamping arms 12, 14. Thus, to transition the clip 10 into the expanded position, the surgeon may use the laparoscopic tool to squeeze the protruding knobs 52 of the first and second clamping arms 12, 14 toward each other, so as to force the proximal first ends 12a, 14a toward each other and force the distal second ends 12b, 14b away from each other. It will be understood that any appropriate term may be used to describe the knobs 52, such as tab, protrusion, protuberance, bump, button and the like.

In another embodiment, the surgeon may use a laparoscopic applicator (not shown) which includes a chamber for storage of a plurality of the clips 10. The clips 10 are positioned within the applicator chamber in the at-rest position and are advanced through the chamber using an actuator (not shown). As each clip 10 advances out of the chamber, each clip 10 is preferably moved from the at-rest position to the expanded position. Alternatively, the clips 10 may exit the applicator chamber in the at-rest position and may have to be manually placed into the expanded position as described above.

In one embodiment, when the clip 10 in the expanded position is properly placed on the patient's tissue 100, the first and second clamping arms 12, 14 are preferably oriented on either side of the incision 110, such that the longitudinal axis $X_1$ of the clip 10 is generally parallel to the direction of extension of the incision 110. The first and second clamping arms 12, 14 may be oriented equidistantly from the incision 110 or may be offset from the center of the incision 110. Also, it will be understood that the clip 10 may be oriented in any direction on the incision 110, as long as the first and second clamping edges 12c, 14c of the clip 10 are positioned to grip the edges of tissue to be brought together.

More preferably, when the clip 10 is properly positioned, the first clamping edge 12c and the teeth 17 of the first clamping arm 12 preferably engage a first edge of the incised tissue 100 and the second clamping edge 14c and the teeth 17 of the second clamping arm 14 preferably engage a second opposing edge of the incised tissue 100. The surgeon may also use any type of appropriate instrument(s) necessary to pull at least a small portion of the incised tissue 100 into the interior cavity 24 of the expanded clip 10. In one embodiment, at least a portion of the interior cavity 24 of the clip 10, and more particularly at least a portion of the internal surfaces 13a, 15a of the sidewalls 13, 15, is coated with an adhesive, such that the tissue 100 will be better secured in the clip 10.

Once the incised tissue 100 is secured within the clip 10, the surgeon preferably utilizes a laparoscopic tool to transition the clip 10 to its contracted position. To do so, the surgeon applies pressure to the exterior surfaces 13b, 15b of the sidewalls 13, 15 of the first and second clamping arms 12, 14 to cause the first and second clamping arms 12, 14 to pivot about the fixed pivot point 20 and move toward each other, until the edges of the incised tissue 100 are compressed between the first and second clamping edges 12c, 14c and the teeth 17 of the clip 10, thereby closing at least a portion of the incision 110. Pressure is also applied to the knobs 52 and/or the exterior surfaces 13b, 15b of the sidewalls 13, 15 of the first and second clamping arms 12, 14 to cause the proximal first ends 12a, 14a at the top 10a of the clip 10 to move toward and be brought into direct engagement with each other. In the embodiment where the pin 22 is held within the first and second apertures 16, 18, this action also causes the first and second ends 22a, 22b of the interference-fit pin 22 to extend through the first and second apertures 16, 18 and outwardly away from the exterior surfaces 13b, 15b of the sidewalls 13, 15 of the first and second clamping arms 12, 14, such that the interference-fit pin 22 transitions into its second arcuate configuration.

In the contracted position of the clip 10, when positioned on the patient's tissue 100, the first and second clamping arms 12, 14 apply positive pressure to the patient's tissue 100 around the incision 110 to hold the tissue 100 together. For certain tissue closures, this position may also support hemostasis. The compressive force necessary to do so is generated remotely from the patient's tissue 100 at the fixed pivot point 20 and the pin 22. The resulting remotely generated force is then transferred through the pin 22 and the first and second clamping arms 12, 14 to the clamped subcutaneous tissue 100. More preferably, the force generated remotely at the fixed pivot point 20 and the pin 22 is transferred into the clamped tissue 100 up to a depth of approximately 1 centimeter. It will be appreciated by those skilled in the art that, by using longer or shorter first and second clamping arms 12, 14, the remotely generated compressive force can be transferred into the clamped tissue 100 from depths of approximately 5 mm to approximately 2 cm, depending on the particular needs of the surgical procedure.

This procedure may then be repeated with as many clips 10 as necessary to close the incision 110 by arranging a plurality of clips 10 side by side (directly adjacent or spaced apart) on the patient's tissue 100 along the entire length of the incision 110. For example, a first clip 10 may be applied to the tissue 100 as described above. Then, a second clip 10 may be applied to the tissue 100 in the same manner and may be positioned immediately adjacent to or at least slightly spaced apart from the first clip 10.

During closure of the wound or incision 110, preferably one or more therapeutic pharmaceutical, antimicrobial or restorative agents may be applied into and/or onto the wound or incision 110. More particularly, in one embodiment, at least a portion of the clip 10 is coated with or otherwise includes any type of agent that may be beneficial in the surgical or post-surgical environment. More preferably at least a portion of the interior surface 13a, 15a of each of the first and second sidewalls 13, 15, and most preferably the entirety of the interior surfaces 13a, 15a, is coated with such an agent. Examples of such agents include adhesives, antibiotics, soaps, degradation-inducing components, anesthetics, healing-promoters (e.g., growth factors or collagens), protectants (e.g., antioxidants), clotting promoters, clotting inhibitors, hyaluronic acid, natural or synthetic plant extracts or distillates, natural or synthetic animal extracts or distillates, natural or synthetic mineral extracts or distillates (e.g., honey, lobelia extracts, saliva proteins, isolated proteins, silver, titanium dioxide or copper antibacterial preparations), bone cements, stem cell preparations, vascular pastes, analgesics, wetting or drying agents (e.g., desiccants, absorbables, foams), heating or cooling agents, staining agents, cosmetic agents, diagnostic agents, shielding agents, and hair growth or retardation agents. Further, such agents may include natural or synthetic bodily tissues, as prepared or combined ingredients, which are actively sprayed, spread or deposited into and/or onto the wound 110 upon closure, or which are passively emitted via decomposition, degradation or activation following the application of the clip 10.

In another embodiment, the clip 10 is used in conjunction with a base sheet (not shown) to further ensure the prevention of scarring that may occur between portions of adjacent tissue. The base sheet is substantially planar in an unused form and is formed of one or more flexible elongated base members (none shown). The base sheet is flexible so that it may conform to the contours of a patient's subcutaneous tissue or internal organs once attached thereto. The base sheet is preferably made of materials that are absorbable by human or animal tissue. For example, the base sheet may be made of, for example, degradable polyesters, degradable polyurethanes, hyaluronic acid, carboxymethylcellulose, hydrolytically-degradable polyester urethane, oxidized regenerated cellulose, nucleic acids, collagen, chitosan, fibrin, or any combinations thereof. It should be understood by those skilled in the art that the base sheet may be made of any appropriate degradable film material.

In use, the one or more base members of the base sheet are oriented along or around the incision 110 either before or after the incision 110 is made. Then, the clip 10 is removably attached to the base sheet. Specifically, the first and second clamping edges 12c, 14c of the clip 10 directly contact the base sheet and clamp the patient's tissue 100.

The clip 10 provides for quick and accurate closure of wounds or incisions made in cutaneous tissue, subcutaneous tissue, including soft tissue, and internal organs, thereby decreasing the risk of infection that is always associated with an open wound. Specifically, the clip 10 may reduce surgery times by up to two or more minutes per inch of incision on the cutaneous tissue (i.e., the skin) and by an even greater amount for incisions on internal tissues. Further, the clip 10 does not exert the high degree of localized stresses as are applied by sutures.

After closure of an incision, there is no need to remove the clip 10. The clip 10 remains in place during the healing process because it is self-dissolving or bio-absorbable. Specifically, the clip 10 remains adhered to the tissue and remains in place until the healing process is complete, generally approximately fourteen days.

The clip 10 begins to dissolve or degrade over the course of months. As each clip 10 dissolves or degrades, the shape of the clip 10 does not change. Initially, however, while the overall size of the first and second clamping arms 12, 14 begins to decrease, the interference-fit pin 22 initially swells. As such, in one embodiment, during at least the initial stages of degradation of the clip 10, the clip 10 preferably maintains a strong clamping force on the patient's tissue 100. Subsequently, however, as the clip 10 begins to degrade further, the clip 10 begins to lose its clamping force. Also, the clip 10 lacks any exposed sharp edges, such that there is no risk of harm by such edges to the patient's tissue. The clip 10 is also relatively simple to use and can be applied by a surgeon without any assistance.

The clip 10 is ultimately passively removed or released from the patient's body by a normal breakdown of the clip 10. If the clip 10 is used to close subcutaneous or internal tissue, it may degrade by hydrolysis. If the clip 10 is used to close an incision on cutaneous tissue, it may also be actively removed or passively released from the tissue through a natural sloughing of the cutaneous tissue.

It will be appreciated by those skilled in the art that changes could be made to the above described preferred embodiment of the clip 10 without departing from the broad inventive concepts thereof. It is understood, therefore, that this invention is not limited to the particular embodiments disclosed, but is intended to cover modifications within the spirit and scope of the present invention as defined by the appended claims.

We claim:

1. A wound closure device for closing a surgical wound, the device comprising:
    at least one clip for applying pressure to a patient's tissue, the at least one clip comprising: a first clamping arm and a second clamping arm, each of the first and second clamping arms having a proximal first end, an opposing distal second end and a sidewall extending therebetween, each sidewall having an interior surface and an exterior surface, the exterior surface of each sidewall generally extending in a first plane; and
    at least one clamping tooth provided at the distal second end of each of the first and second clamping arms, the at least one clamping tooth having a first leading surface, a second trailing surface opposed to the first leading surface, a base and a clamping tip opposed to the base, the leading surface generally extending at an angle of approximately 50° to 60° with respect to the first plane and the clamping tip generally extending at an angle of approximately 5° to 15° with respect to the first plane.

2. The wound closure device according to claim 1, wherein the base generally extends at the same angle as the clamping tip and the trailing surface generally extends at the same angle as the leading surface with respect to the first plane.

3. The wound closure device according to claim 1, wherein when the at least one clip is applied to a patient's tissue, the first leading surface of the at least one clamping tooth generally extends at an angle of approximately 60° to 75° with respect to the patient's tissue and the clamping tip of the at least one clamping tooth generally extends an angle of approximately 15° to 30° with respect to the patient's tissue.

* * * * *